United States Patent
Jugl et al.

(10) Patent No.: US 9,486,586 B2
(45) Date of Patent: Nov. 8, 2016

(54) DRUG DELIVERY DEVICE AND METHOD FOR DETECTING A CONTACT

(71) Applicant: SANOFI-AVENTIS DEUTSCHLAND GMBH, Frankfurt am Main (DE)

(72) Inventors: Michael Jugl, Frankfurt am Main (DE); Axel Teucher, Frankfurt am Main (DE)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 0 days.

(21) Appl. No.: 14/421,019

(22) PCT Filed: Aug. 15, 2013

(86) PCT No.: PCT/EP2013/067058
§ 371 (c)(1),
(2) Date: Feb. 11, 2015

(87) PCT Pub. No.: WO2014/029681
PCT Pub. Date: Feb. 27, 2014

(65) Prior Publication Data
US 2015/0224265 A1    Aug. 13, 2015

(30) Foreign Application Priority Data

Aug. 20, 2012 (EP) .................................. 12180958

(51) Int. Cl.
*A61M 5/315* (2006.01)
*A61M 5/31* (2006.01)
(Continued)

(52) U.S. Cl.
CPC ....... *A61M 5/31515* (2013.01); *A61M 5/3146* (2013.01); *G01B 5/146* (2013.01); *G01M 13/04* (2013.01); *A61M 2205/3306* (2013.01); *A61M 2205/3327* (2013.01); *A61M 2205/583* (2013.01)

(58) Field of Classification Search
CPC ................ A61M 5/31515; A61M 2205/3327; A61M 2205/3306; A61M 2205/583; A61M 5/315; A61M 5/31511
See application file for complete search history.

(56) References Cited

U.S. PATENT DOCUMENTS

2001/0034506 A1    10/2001  Hirschman et al.
2001/0047153 A1*   11/2001  Trocki .............. A61M 5/14546
                                                                    604/155
(Continued)

FOREIGN PATENT DOCUMENTS

EP    1974761    10/2008
WO    03/101527   12/2003
(Continued)

OTHER PUBLICATIONS

International Search Report for Int. App. No. PCT/EP2013/067058, completed Mar. 6, 2014.

*Primary Examiner* — Kevin C Sirmons
*Assistant Examiner* — Amber Stiles
(74) *Attorney, Agent, or Firm* — McDonnell Boehnen Hulbert & Berghoff LLP

(57) ABSTRACT

The present invention is directed to a drug delivery device with a drive mechanism including a piston rod with a bearing for driving a bung in a cartridge in a distal direction. A movable element is disposed displacably in an axial direction within the drive mechanism. The moveable element is movable between a first position in which a distal end of said movable element protrudes from said bearing and a second position in which a distal end of said movable element lies flush with the distal end of said bearing. The invention is further directed to a method for detecting the contact between the bearing and the movable bung.

15 Claims, 2 Drawing Sheets

(51) Int. Cl.
*G01B 5/14* (2006.01)
*G01M 13/04* (2006.01)

(56) References Cited

U.S. PATENT DOCUMENTS

2004/0254526 A1   12/2004   Weston
2009/0326459 A1*  12/2009   Shipway .......... A61M 5/14566
                                                          604/155
2010/0217188 A1*  8/2010    Lampropoulos .. A61M 25/1018
                                                          604/97.03
2011/0245780 A1   10/2011   Helmer et al.

FOREIGN PATENT DOCUMENTS

WO   2010/124961   11/2010
WO   2011/039226   4/2011
WO   2011/039229   4/2011

* cited by examiner

DRUG DELIVERY DEVICE AND METHOD FOR DETECTING A CONTACT

CROSS REFERENCE TO RELATED APPLICATIONS

The present application is a U.S. National Phase Application pursuant to 35 U.S.C. §371 of International Application No. PCT/EP2013/067058 filed Aug. 15, 2013, which claims priority to European Patent Application No. 12180958.6 filed Aug. 20, 2012. The entire disclosure contents of these applications are herewith incorporated by reference into the present application.

TECHNICAL FIELD

The present invention is directed at a drug delivery device comprising a cartridge with a movable bung and a drive mechanism including a piston rod with a bearing at a distal end for driving the bung in a distal direction for delivering a medicament such as insulin. The invention is further directed at a method for detecting a contact between the bearing and the movable bung.

BACKGROUND

Pen type drug delivery devices have applications where regular injection by persons without formal medical training occurs. This is increasingly common among patients having diabetes or the like. Self-treatment enables such patients to conduct effective management of their disease. The injection pens usually comprise a housing in which the drive mechanism is located. Some kinds of drug delivery devices also comprise a compartment to accommodate a cartridge in which the medicament is received. With the drive mechanism, the bung in the cartridge is displaced for dispensing the medicament accommodated therein. The drive mechanism includes a piston rod that has a bearing at one end, wherein the bearing is arranged in such manner such that it faces the bung. With the piston rod, the bearing is displaced toward the bung and urges the bung toward a distal end of the drug delivery device, which is closest to the dispensing end (needle end) of the device. Medicament from the cartridge is dispensed thereby. The opposite side of the device is referred to as the proximal end.

In devices of the generic kind, the manufacture may bring unavoidable tolerances and functional clearances between the single components of the drug delivery device, in particular the drive mechanism. As a consequence, clearances such as a gap between the elements of the drive mechanism, such as between the bearing and the cartridge bung may occur even after the drug delivery device has been assembled so that the bung may not be in contact with the distal end of the bearing. It is, therefore, important to eliminate the gap between the cartridge bung and the distal end of the bearing and to bring the drive mechanism in a prestressed state prior to use. Otherwise, it would be possible that the dialed dose may not be dispensed from the device correctly. Initial clearances may already falsify the setting of the dose. To adjust the drug delivery device for use, priming actions are conducted to ensure that the drive mechanism is correctly adjusted, e.g. that the drive mechanism is in contact with the bung so that the correct amount of the medicament can expelled from the device. These actions often come along with a small amount of medicament being dispensed which gives a visual indication that the drug delivery device is ready to use.

It is known in the art to conduct adjustment of the drug delivery device by measurement of the bearing and the bung position before pressing, resp. assembly. The parts are then adjusted according to the measured value such that the bearing is brought into contact with the bung. However, the assembly machines for this method are expensive and the required time cycle is very long.

SUMMARY

It is an object of the present invention to simplify the adjustment process in a drug delivery device. This is obtained by a drug delivery device as claimed in claim 1 as well as by a method as defined in claim 12.

The present invention is based on the idea to detect the contact between the drive mechanism and the bung in the cartridge. A movable element is disposed displaceably in axial direction within the drive mechanism. The movable element is of a certain predetermined or premeasured length and may be movable between a first position in which a distal end of the movable element protrudes from the bearing and a second position in which the distal end of the movable element lies flush with the distal end, respectively a distal end surface of the bearing.

In other words, it is the main concept of the present invention to place a pin or the like moveable element e.g. in the middle of the lead screw or piston rod. As the length of the pin is known, the overlap can be measured and so the distance between the bearing and the bung calculated. The distance is known and can be adjusted with the angle of rotation.

By initially protruding from the bearing in distal direction, the movable element can be urged in proximal direction by the bung, when the drive mechanism approaches the bung. Once the bearing makes contact with the bung, the distal end of the movable element lies flush or substantially flush with the distal end surface of the bearing and, consequently, the position of the proximal end of the movable element with respect to the distal surface end of the bearing is clearly determined. The length, the movable element extends from the distal bearing surface in proximal direction can be used as an indicator for the moment, the bearing makes contact with the bung. When a specific distance between e.g. the proximal end of the movable element and the bearing surface is reached, the moment the bearing contacts the bung is also indicated. An easy and reliable indication of the contact is possible thereby.

Preferably, the movable element is configured such that it overlaps (protrudes) the drive mechanism in proximal direction when the bearing contacts the bung. This arrangement provides for an easy and yet reliable way to capture confirmation that the contact is made. It is, however, not necessary to take into account the ends of the movable element in the context of a confirmation. For example, the drive mechanism and the movable element can each be provided with visual or any other indicators distributed on predetermined position so that the relative movement between the movable element and the drive mechanism is visually presented and/or can be easily acquired by measuring means.

For example, the movable element may comprise markings or a scale that are readable by a camera, e.g. Relative movement between the movable element and the drive mechanism can be measured in observing the intersection of the proximal end of the drive mechanism and the movable element.

Alternatively, a laser beam may be used to measure the distance to the proximal end of the movable element on one hand and the distance to the proximal end of the drive mechanism on the other hand. Relative movement between the movable element and the drive mechanism can be determined in calculating the difference between the two distances and comparing the calculated differences of at least two measurements.

According to one embodiment, the drive mechanism may be at least partly surrounding the movable element. The length of the drive mechanism or at least the piston rod may preferably be shorter than the length of the movable element. In another preferred embodiment, the movable element may be disposed in a center hole extending through the bearing in axial direction providing for a compact structure.

In order to ensure easy capture of the information regarding the position of the movable element relative to the drive mechanism, the movable element may extend through the piston rod. Preferably, the movable element is a pin which may be aligned substantially concentrically with the longitudinal axis of the drive mechanism.

A further embodiment of the drug delivery device may include a lead screw as a piston rod. According to one further embodiment of the invention, the lead screw can be in threaded engagement with a body. Advantageously, the body is at least partly surrounding the lead screw.

In further developing the concept the invention is based on, the lead screw and the body can be connected to each other in such manner that position of the bearing relative to the bung can be adjusted or regulated by applying torque to the lead screw or to the body. A gap or a clearance between the bearing and the bung can be reliably adjusted by rotation, providing for a more precise definition of the forward motion of the bearing relative to the cartridge bung.

According to a further embodiment of the invention, the movable element may be provided detachable in the drive mechanism enabling removal of the pin after the drug delivery device is adjusted.

It is preferred, when the cartridge contains a medicament such as insulin.

The drug delivery device can be a disposable injection device. Such devices can be thrown away or recycled after the content of the medicament has been exhausted. However, the present invention is also applicable with re-usable devices designed to replace an emptied cartridge with a filled one after the whole content of the former cartridge has been administered.

An example of a disposable device in which the present invention may be used is given in EP 1 974 761 A2.

The object of the present invention is further achieved by a method for detecting the contact between the bearing and the movable bung, wherein the contact is indicated by a predetermined or certain distance between a measuring point on the movable element and a further measuring point e.g. outside the device or on the drive mechanism. The method includes the steps of providing the displaceable movable element within the drive mechanism such that it protrudes from the bearing in distal direction. Preferably, the movable element has a known length and the drive mechanism or one of its components, e.g. the piston rod, has a known length, too. Then, the bearing is displaced relative to the bung such that a gap or a clearance between the bearing and the bung is gradually reduced. The relative distance between the measuring point on the drive mechanism and the measuring point on the movable element is measured. As a certain distance between the measuring point on the drive mechanism and the measuring point on the movable element corresponds to a gap of the length zero, contact between the bearing and the bung is indicated the moment, the corresponding distance is set.

Preferably, the contact is indicated by a predetermined overlap between the drive mechanism and the movable element. The overlap can be either a positive or a negative overlap, wherein the moveable element may overlap the drive mechanism or the drive mechanism may overlap the movable element. The overlap can also be zero, which means that the measuring points lie directly adjacent to each other when the contact is made.

It is preferred that the overlap is a positive overlap with the movable element protruding from a proximal end of the drive mechanism in proximal direction, a specific length of the overlap directly indicating the moment of contact.

Preferably, the distance between the bearing and the bung is adjusted by rotational movement of a drive mechanism element such as a lead screw or by a body which may be threadedly engaged with the lead screw. This provides for a very accurate adjustment of the gap between the bearing and the bung. The moveable element can be detached after the contact between the bearing and the bung is indicated, as the drug delivery device is now set for later use.

The term "medicament", as used herein, means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N- palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyhepta¬ decanoyl) human insulin.

Exendin-4 for example means Exendin-4(1-39), a peptide of the sequence H His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4 (1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4 (1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(02)25] Exendin-4 (1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(02)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2) 25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2) 25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

BRIEF DESCRIPTION OF THE FIGURES

In the following, the invention will be described by way of an example according to one embodiment of the invention and with reference to the schematic drawings in which.

DETAILED DESCRIPTION

Figure 1:
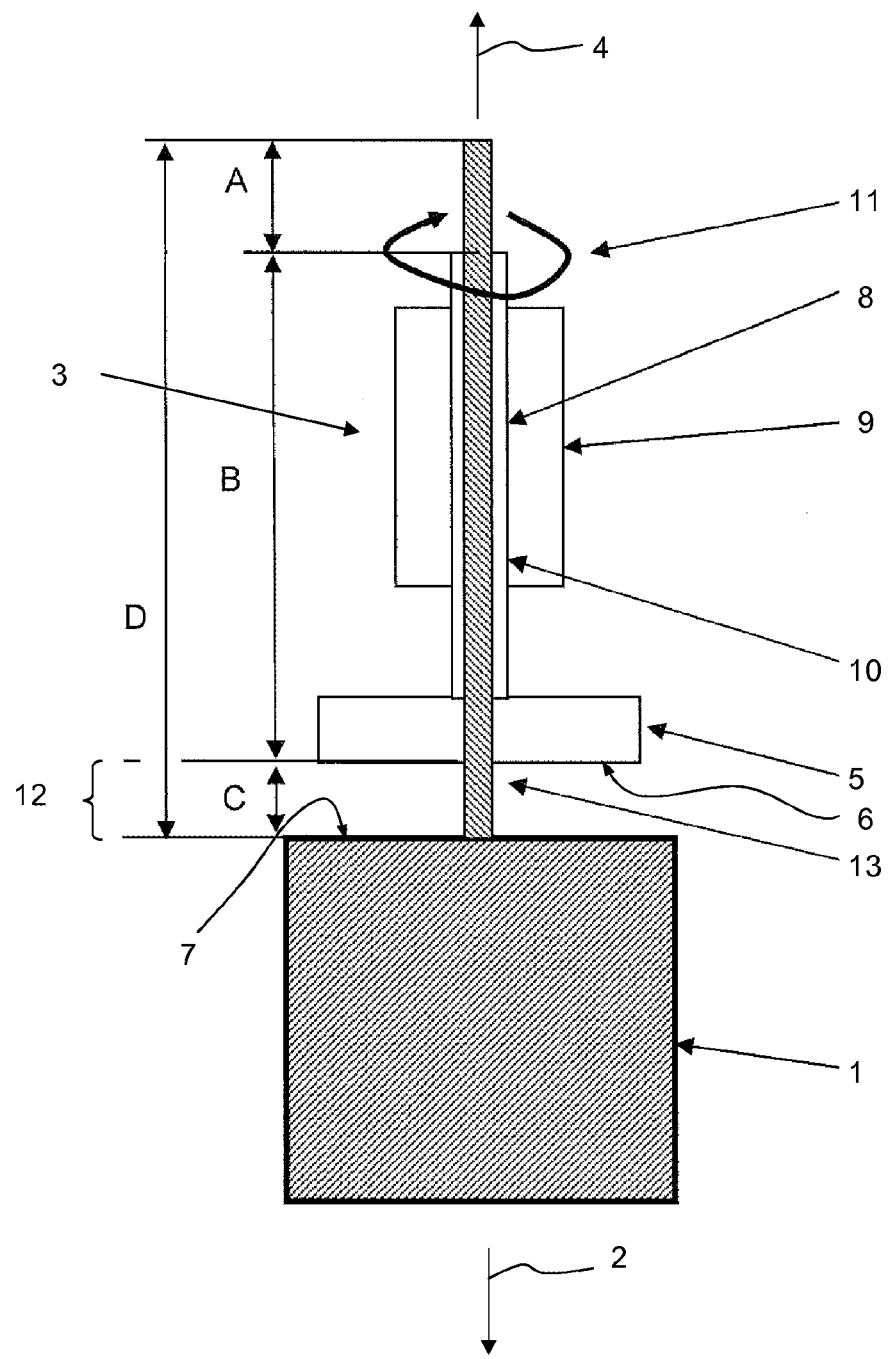
FIG. 1 schematically displays in a side view the drive mechanism of a drug delivery device for displacing a cartridge bung with the movable element in a start position.

FIG. 1 shows a cartridge bung 1 for expelling a medicament out of a cartridge (not shown) in a distal direction 2. A distal movement of the cartridge bung is induced by a drive mechanism 3 located in proximal direction 4 from the cartridge bung 1. The drive mechanism 3 comprises a bearing 5 with a distal end surface 6 facing a proximal end surface 7 of the cartridge bung 1.

In proximal direction 4, from the bearing 5, a lead screw 8 is arranged, said lead screw 8 being connected or coupled to the bearing 5 in such manner, that a movement of the lead screw 8 in distal direction moves the bearing 5 in the same direction. The lead screw 8 is of an elongated shape and extends from the bearing 5 in proximal direction. A proximal section of the lead screw 8 is surrounded by a body 9, wherein the lead screw 8 and the body 9 are connected to each other via a thread connection 10. The thread connection 10 between the lead screw 8 and the body 9 is configured such that a relative rotation between the elements 8 and 9 results in a translational movement of the lead screw 8 relative to the body 9 in proximal or distal direction. As an example, by applying torque to the lead screw 8 in the direction indicated by arrow 11, the lead screw 8 screws through the body 9 in distal direction thereby displacing the bearing 5 toward the bung 1.

During manufacture of the device, the bearing 5 and the cartridge bung 1 are mounted such they are spaced apart from each other with a clearance, i.e. with a gap 12 of the length C between the distal end surface 6 of the bearing 5 and the proximal end surface 7 of the bung 1. The length C is usually not known and may vary, e.g. due to tolerances.

A pin 13 is disposed displaceably in axial direction (proximal or distal direction) in the drive mechanism 3. The lead screw 8 and the bearing 5 each have a continuous center hole extending from the proximal end of the drive mechanism to the distal end of the drive mechanism with the pin 13 located therein so that the pin 13 is substantially concentrically aligned with a longitudinal axis of the lead screw 8. The pin 13 can shift in proximal or in distal direction with respect to the lead screw 8 and the bearing 5. The pin 13 is of the length D while the drive mechanism with the lead screw 8 and the bearing 5 is of the length B. Each of the lengths D and B are known values.

As FIG. 1 further shows, the pin 13 is substantially longer than the drive mechanism 3 (D>B). The pin 13 is arranged within the drive mechanism such that its distal end protrudes from the distal end surface 6 of the bearing in direction of the proximal end surface 7 of the bung. This is a first position of the pin 13 relative to the drive mechanism 3. In the position shown, the distal end of the pin 13 contacts the bung 1. A proximal end of the pin 13 protrudes from the proximal end of the drive mechanism over the length A. With the known values D and B, the gap can be calculated by measuring the overlap A wherein the gap C=D−B−A.

Pin 13 comprises markings or a scale (not shown). The markings or scale are readable by a camera, e.g. The camera observes the intersection of the proximal end of the drive mechanism and the movable element and a respective value is read from the scale on pin 13 when in the first position. The value corresponds to the overlap, i.e. the amount by which pin 13 protrudes from the proximal end of the drive mechanism. Knowing the values B and D from the construction of the device and having determined value A, value C, the gap, thus can be calculated.

Alternatively, a laser beam may be used to measure the distance to the proximal end of pin 13 on one hand and the distance to the proximal end of the drive mechanism on the other hand. Calculating the difference between the two distances provides value A. Thus, knowing the values B and D from the construction of the device and having determined value A, value C, the gap, can be calculated.

When the bearing 5 moves relative to the bung 1 by e.g. displacing the drive mechanism 3 toward the cartridge bung 1, the pin 13 is urged in proximal direction by the proximal end surface 7 of the bung 1 and through the drive mechanism 3 until the cartridge bung 1 makes contact with the bearing 5. This second position is shown in FIG. 2.

Figure 2:
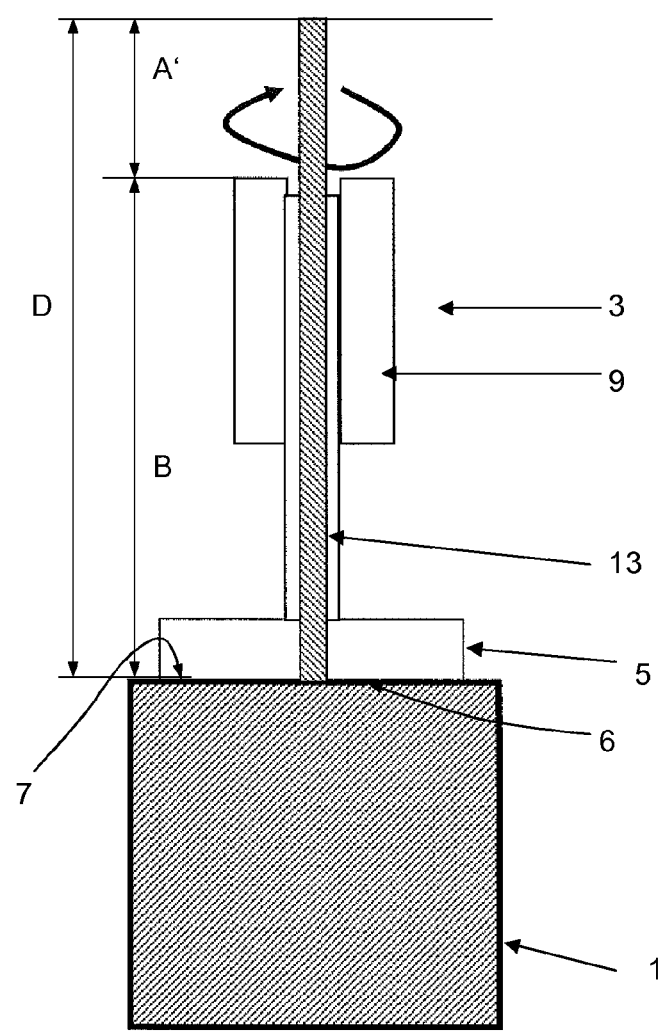
FIG. 2 shows the movable element of FIG. 1 in an end position after adjustment.

As can be taken from FIG. 2, the gap 12 of FIG. 1 between the bearing 5 and the cartridge bung 1 has been eliminated, wherein the distal end surface 6 of the bearing 1 now contacts the proximal end surface 7 of the bung 1. As the pin 13 has been moved in proximal direction in correspondence to the movement of the cartridge bung 1 relative to the bearing 5, the pin 13 now protrudes from the proximal end of the drive mechanism 3 with the length A', while the distal end lies flush with the distal end surface 6 of the bearing 5. As the gap has been eliminated, A' corresponds to the difference between the lengths B and D. Hence, the moment, the bung 1 makes contact with the bearing 5 is the moment, when the pin 13 overlaps the drive mechanism 3 by the pre-known length A'. During the adjustment process, the length of the overlap between the pin 13 and the drive mechanism 3 can be measured, respectively monitored. The moment, the length A' is reached, further movement of the drive mechanism in distal direction is stopped as the length A' indicates that the bearing 5 has made contact with the bung 1.

The invention claimed is:

1. A drug delivery device comprising:
a cartridge with a movable bung,
a drive mechanism including a piston rod configured as a lead screw with a bearing at a distal end for driving the bung in a distal direction, and
a movable element, which is disposed displaceably in an axial direction within the drive mechanism,
wherein the moveable element is movable between a first position in which a distal end of said movable element protrudes from said bearing and a second position in which a distal end of said movable element lies flush with the distal end of said bearing,
wherein the movable element is disposed in a center hole extending through the bearing in axial direction.

2. The drug delivery device according to claim 1, characterized in that the movable element is configured such that it overlaps the drive mechanism in a proximal direction when the bearing contacts the bung.

3. The drug delivery device according to claim 1, characterized in that the movable element extends through the piston rod.

4. The drug delivery device according to claim 1, characterized in that the movable element is a pin which is substantially concentrically aligned with the longitudinal axis of the drive mechanism.

5. The drug delivery device according to claim 1 further comprising a body, characterized in that the lead screw is in threaded engagement with said body.

6. The drug delivery device according to claim 5, characterized in that the lead screw and the body are connected to each other in such manner that a position of the bearing relative to the bung can be adjusted by applying torque to the lead screw or to the body.

7. The drug delivery device according to claim 1, characterized in that the movable element is provided detachably in the drive mechanism.

8. The drug delivery device according to claim 1, characterized in that the cartridge contains a medicament.

9. The drug rug delivery device according to claim 1, characterized in that the drug delivery device is a disposable injection device.

10. The drug delivery device according to claim 1, characterized in that the distal end of the bearing is provided to make contact with the bung and to drive the bung in distal

SEQUENCE LISTING

<160> NUMBER OF SEQ ID NOS: 1

<210> SEQ ID NO 1
<211> LENGTH: 39
<212> TYPE: PRT
<213> ORGANISM: Artificial Sequence
<220> FEATURE:
<223> OTHER INFORMATION: Synthetic

<400> SEQUENCE: 1

```
Ser Pro Pro Pro Ala Gly Ser Ser Pro Gly Gly Asn Lys Leu Trp Glu
1               5                   10                  15

Ile Phe Leu Arg Val Ala Glu Glu Glu Met Gln Lys Ser Leu Asp Ser
            20                  25                  30

Thr Phe Thr Gly Glu Gly His
            35
``` direction, wherein the movable element is in the second position when the bearing makes contact with the bung.

11. A method for detecting a contact between a bearing and a moveable bung in a drug delivery device according to claim 1,
wherein the contact between the bearing and the bung is indicated by a predetermined distance between a measuring point on the movable element and a measuring point on the drive mechanism, said method including the steps of:
providing the displaceable movable element within the drive mechanism such that it protrudes from the bearing in a distal direction;
displacing the bearing relative to the bung such that a gap between the bearing and the bung is reduced; and
measuring the relative distance between the measuring point on the drive mechanism and the measuring point on the movable element.

12. The method according to claim 11, characterized in that a predetermined overlap between the drive mechanism and the movable element indicates the contact between the bearing and the bung.

13. The method according to claim 11, characterized in that a pin is detached after contact between the bearing and the bung is indicated.

14. A method for assembling a drug delivery device using the method of claim 11 to detect contact between the bearing and the bung.

15. A drug delivery device comprising:
a cartridge with a movable bung,
a drive mechanism including a piston rod configured as a lead screw with a bearing at a distal end for driving the bung in a distal direction, and
a movable element, which is disposed displaceably in an axial direction within the drive mechanism,
wherein the moveable element is movable between a first position in which a distal end of said movable element protrudes from said bearing and a second position in which a distal end of said movable element lies flush with the distal end of said bearing,
wherein the movable element is disposed in a center hole extending through the bearing in axial direction, and
wherein in the first position the distal end of the movable element contacts the bung and a proximal end of the movable element protrudes from the proximal end of the drive mechanism over a length A.

* * * * *